(12) United States Patent
Makarov

(10) Patent No.: US 9,753,011 B2
(45) Date of Patent: Sep. 5, 2017

(54) APPARATUS AND METHODS FOR ION MOBILITY SPECTROMETRY

(71) Applicant: Thermo Fisher Scientific (Bremen) GmbH, Bremen (DE)

(72) Inventor: Alexander Makarov, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 14/947,119

(22) Filed: Nov. 20, 2015

(65) Prior Publication Data

US 2016/0084799 A1  Mar. 24, 2016

Related U.S. Application Data

(63) Continuation of application No. 14/379,235, filed as application No. PCT/EP2013/052994 on Feb. 14, 2013, now Pat. No. 9,207,206.

(30) Foreign Application Priority Data

Feb. 21, 2012  (GB) .................................. 1202895.7

(51) Int. Cl.
*G01N 27/62* (2006.01)
*H01J 49/00* (2006.01)
*H01J 49/24* (2006.01)
*H01J 49/06* (2006.01)

(52) U.S. Cl.
CPC .......... *G01N 27/622* (2013.01); *H01J 49/004* (2013.01); *H01J 49/0031* (2013.01); *H01J 49/061* (2013.01); *H01J 49/063* (2013.01); *H01J 49/24* (2013.01)

(58) Field of Classification Search
CPC combination set(s) only.
See application file for complete search history.

(56) References Cited

U.S. PATENT DOCUMENTS

| 6,707,037 B2 * | 3/2004 | Whitehouse | H01J 49/0095 250/287 |
| 6,888,130 B1 * | 5/2005 | Gonin | H01J 49/027 250/281 |
| 2006/0054918 A1 * | 3/2006 | Lohokare | H01L 31/0304 257/103 |
| 2007/0029473 A1 * | 2/2007 | Verentchikov | H01J 49/406 250/281 |
| 2010/0327157 A1 | 12/2010 | Green et al. | |
| 2011/0291001 A1 * | 12/2011 | Hoyes | H01J 49/0081 250/283 |

(Continued)

FOREIGN PATENT DOCUMENTS

| CN | 1689134 A | 10/2005 |
| CN | 101421817 A | 4/2009 |

(Continued)

*Primary Examiner* — Phillip A Johnston
*Assistant Examiner* — Hsien Tsai
(74) *Attorney, Agent, or Firm* — David A. Schell

(57) ABSTRACT

A method of ion mobility spectrometry wherein ions undergo multiple stages of ion mobility separation and multiple stages of inertial ion motion wherein the mean free path between ion collisions with gas is significantly longer than in the stages of ion mobility separation, wherein each stage of inertial ion motion lies between successive stages of ion mobility separation.

26 Claims, 6 Drawing Sheets

(56) References Cited

U.S. PATENT DOCUMENTS

2011/0300552 A1    12/2011  Demirev et al.

FOREIGN PATENT DOCUMENTS

| | | | |
|---|---|---|---|
| CN | 101584021 | A | 11/2009 |
| CN | 101213633 | A | 1/2011 |
| GB | 2440970 | A | 2/2008 |
| GB | 2447330 | A | 9/2008 |
| GB | 2448203 | A | 10/2008 |
| GB | 2457556 | A | 8/2009 |
| GB | 2464176 | A | 4/2010 |
| GB | 2486584 | A | 6/2012 |
| JP | 2005-079049 | A | 3/2005 |
| JP | 2009-516327 | A | 4/2009 |
| WO | WO 2004/008481 | A1 | 1/2004 |
| WO | WO 2005/001878 | A2 | 1/2005 |
| WO | WO 2006/103448 | A2 | 10/2006 |
| WO | 2007054712 | A2 | 5/2007 |
| WO | WO 2007/122383 | A2 | 11/2007 |
| WO | WO 2008/071921 | A2 | 11/2007 |
| WO | WO 2008/028159 | A2 | 3/2008 |
| WO | WO 2010/020763 | A2 | 2/2010 |

* cited by examiner

APPARATUS AND METHODS FOR ION MOBILITY SPECTROMETRY

CROSS-REFERENCE TO RELATED APPLICATIONS

The present application is a continuation under 35 U.S.C. §120 and claims the priority benefit of co-pending U.S. patent application Ser. No. 14/379,235, filed Aug. 15, 2014, which is a National Stage application under 35 U.S.C. §371 of PCT Application No. PCT/EP2013/052994, filed Feb. 14, 2013. The disclosures of each of the foregoing applications are incorporated herein by reference.

FIELD OF THE INVENTION

This invention relates to apparatus and methods for ion mobility spectrometry (IMS). The apparatus and methods are suitable for use in combination with mass spectrometry (MS), e.g. in hybrid IMS/MS instruments.

BACKGROUND OF THE INVENTION

Known ion mobility spectrometers typically comprise a drift tube wherein ions are caused to drift through a space under the influence of a constant applied electric field. Various constructions of drift tube have been proposed. The drift tube may, for example, comprise a series of ring electrodes axially spaced apart along the length of the spectrometer, wherein a constant potential difference is maintained between adjacent ring electrodes such that a constant electric field is produced in the axial direction. A pulse of ions is introduced into the drift tube, which contains a buffer gas, and as the ions travel through the tube under the influence of the constant electric field they attain a constant drift velocity and separate in the axial direction according to their ion mobility. The buffer gas is often arranged flowing in the opposite direction to the direction of ion travel.

An ion mobility spectrometer may be operated on its own as a means for ion separation or it may be used in combination with other ion separation devices in so-called hybrid IMS instruments. Examples of hybrid IMS instruments include those based on liquid chromatography IMS (LC-IMS), gas chromatography IMS (GC-IMS) and IMS mass spectrometry (IMS-MS). The latter type of instrument is a powerful analytical tool which employs mass spectrometry for further separating and/or identifying peaks in an ion mobility spectrum. More than two separation techniques may be combined, e.g., LC-IMS-MS.

Ion mobility spectrometers may be operable at atmospheric pressure (see e.g. U.S. Pat. No. 5,162,649) and can offer a resolution of up to 150 (see e.g. Wu et al., Anal. Chem. 1998, 70, 4929-4938). However, operation at lower pressures is more suitable for hybrid IMS-MS instruments (see e.g. U.S. Pat. No. 5,905,258 and WO01/64320) to increase speed of separation and reduce ion losses. Operation of the ion mobility spectrometer at lower pressures frequently leads to greater diffusion losses and lower resolution. In order to counter the problem of diffusion losses, an RF pseudo-potential well may be arranged in the drift tube to confine ions radially so that it acts as an ion guide and may be used to transport ions efficiently (see e.g. U.S. Pat. No. 6,630,662).

In a modification to an ion mobility spectrometer, U.S. Pat. No. 6,914,241 describes how ions may be separated according to their ion mobility by progressively applying transient DC voltages along the length of an ion mobility spectrometer or RF ion guide comprising a plurality of axially spaced apart electrodes. The ion mobility spectrometer may comprise an RF ion guide such as a multipole rod set or a stacked ring set. The ion guide is segmented in the axial direction so that independent transient DC potentials may be applied to each segment. The transient DC potentials are superimposed on top of an RF voltage which acts to confine the ions radially and/or any constant DC offset voltage. The transient DC potentials thereby generate a so-called travelling wave which moves along the length of the ion guide in the axial direction and which acts to move ions along the length of the ion mobility spectrometer.

In the above types of ion mobility spectrometers, ions are propelled along the ion guide and ions may be separated according to their ion mobility. However, in order to achieve a high resolution or resolving power of ion mobility separation at relatively low pressures, a relatively long drift tube must be employed in order to keep within the so-called low field limit as described in more detail below.

In order to separate ions along the axial direction according to their ion mobility in an RF ion guide, an axial DC electric field may be generated which is orthogonal to the radial RF field for radial confinement. If a constant axial electric field E is applied in order to move ions along and through an ion guide containing a gas, then the ion will acquire a characteristic velocity, v according to:

$$v = E*K \quad \text{(eqn. 1)}$$

wherein K is the ion mobility.

In order to maintain ion mobility separation in the so called low field regime wherein ions do not receive significant kinetic energy from the driving field, the ratio of E (in V/m) to the pressure of the background gas P (in mbar) should be maintained at a value less than about 200V/(m*mbar). At the same time, resolving power, R, of separation according to ion mobility (FWHH) is limited by diffusion and can be approximately estimated as:

$$R = \frac{1}{2}\sqrt{\frac{ezEL}{kT}} \quad \text{(eqn. 2)}$$

wherein z is the charge state of ions, L is the length of separation (m), T is temperature (degrees Kelvin) of background gas, e is the elementary charge ($1.602*10^{-19}$ Coulomb) and k is Boltzmann's constant ($1.38*10^{-23}$ J/K). More accurate calculations can be found, e.g., in G. E. Spangler, "Expanded Theory for the resolving power of a linear ion mobility spectrometer", *Int. J. Mass Spectrom.* 220 (2002) 399-418. As increase of E is limited by low-field conditions and decrease of T is associated with cumbersome cryogenic techniques, it can be seen that the only way towards achieving higher R is to increase the separation length L. However, increasing the separation length can be problematic since space is typically limited.

One solution to the problem of increasing the separation length proposed in the prior art of WO2008/104771, GB2447330 and GB2457556 is to coil the ion mobility drift tube. However, construction of the drift tube becomes complex in that case and precludes rapid transfer of ions through the spectrometer in the case when no mobility separation is required.

A compact ion mobility spectrometer is disclosed in WO2008/028159 and US2011/121171 that has a multi-turn or racetrack configuration in which the ions follow a closed circular path. Only a narrow range of ion mobilities is retained on a circular trajectory but resolving power could reach many hundreds. Again, the construction of the drift tube becomes complex.

In view of the above background, the present invention has been made.

SUMMARY OF THE INVENTION

According to an aspect of the present invention there is provided a method of ion mobility spectrometry comprising: (i) introducing a packet of ions into a drift space; (ii) passing the ions through the drift space wherein the ions separate according to their ion mobility; and (iii) reflecting or deflecting the ions that have passed through the drift space back into the drift space wherein the ions can further separate according to their ion mobility. The reflecting or deflecting takes place in a region at lower pressure than the drift space.

According to another aspect of the present invention there is provided an ion mobility spectrometer comprising: a drift space for separating ions from an ion source according to their ion mobility; and an ion mirror or deflector for receiving ions that have passed through the drift space and reflecting or deflecting the ions back into the drift space to pass again through the drift space. The ion mirror or ion deflector is located in a region at lower pressure than the drift space.

According to yet another aspect of the present invention there is provided an ion mobility spectrometer comprising a drift space for separating ions according to their ion mobility and at least one ion mirror or at least one ion deflector located adjacent one or both of the ends of the drift space for receiving ions from the drift space and returning the ions into the drift space, the pressure in the region of the ion mirror(s) or ion deflector(s) being such that separation of the ions according to their ion mobility does not occur in that region.

According to a further aspect of the present invention there is provided a method of ion mobility spectrometry wherein ions undergo multiple stages of ion mobility separation and multiple stages of inertial ion motion wherein the mean free path between ion collisions with gas in the stages of inertial ion motion is significantly longer than in the stages of ion mobility separation, wherein each stage of inertial ion motion lies between successive stages of ion mobility separation.

According to a still further aspect of the present invention there is provided an ion mobility spectrometer comprising: one or more drift spaces for separating ions according to their ion mobility; and one or more regions for allowing the ions to undergo inertial ion motion wherein their mean free path between collisions with gas is significantly longer than in the one or more drift spaces, wherein each of the one or more regions is configured to receive the ions from one of the one or more drift spaces and comprises ion optics to direct the ions into the same or another one of the one or more drift spaces, whereby each of the one or more drift spaces is arranged to be passed through multiple times by the ions.

In accordance with the present invention, the drift space (herein meaning each drift space wherein there are two or more drift spaces) may be utilized at least twice for ion mobility separation of the ions, e.g. at least once in a first direction and at least once in a second direction (preferably opposite to the first direction), or each time in the same direction. The same drift space is thus re-utilized to enable high resolution of separation by ion mobility. The first and second directions of ion travel being in opposite directions to each other may be regarded respectively as forward and reverse directions. In one type of embodiment, therefore, the invention comprises reflecting or deflecting the ions that have passed through the drift space in a first direction back into the drift space in a second direction opposite to the first direction whereby the ions may further separate according to their ion mobility.

Preferably, the drift space is re-used multiple times. More preferably, after step (iii), the method comprises repeating step (ii) and then (iii) in turn as many times as needed to attain a required ion separation length or resolving power.

Preferably, there are multiple regions of inertial ion motion, i.e. multiple regions comprising ion optics to direct the ions from a drift space into the same or another drift space. Preferably there is such a region at either end of the drift space in the axial direction.

The drift space is preferably located within a drift tube. The drift space, and hence drift tube, is typically elongated along a longitudinal axis referred to herein as being the axial direction. The ions typically enter the drift space through an entry at one end of the drift space and leave the drift space through an exit at the other end of the drift space. The drift space is preferably located within an elongated ion guide. The drift space is most preferably elongated substantially linearly (i.e. straight) in the longitudinal direction although in some embodiments it may be curved. The drift space is preferably a gas filled drift space, i.e. filled with a buffer gas. The drift space may be filled to atmospheric pressure to effect atmospheric pressure ion mobility separation, or at elevated pressure. In other applications, reduced gas pressures may be used in the gas filled drift space, e.g. from 0.01 to 1000 mbar, or 0.01 to 100 mbar, or 0.01 to 10 mbar, preferably in the range 0.01 to 3 mbar. The gas pressure in the gas-filled drift space is preferably 0.01 mbar or higher. Reduced gas pressures are preferred in hybrid IMS-MS instruments. Buffer gases typically used in IMS may be used, such as air or helium for example.

Preferably, to reduce diffusion losses in operation at reduced pressures, an RF pseudo-potential well is arranged in the drift space to confine the ions radially therein. The path of the ions through the drift space may be located within an RF ion guide, preferably an RF multipole ion guide, i.e. an ion guide comprising a plurality of multipole rods to produce, for example, a quadrupole, hexapole or octapole field. As alternatives to a multipole, ion tunnels, ion funnels or other devices may be used to define the ion path through the drift space, for example comprising a series of axially spaced apart ring electrodes (stacked rings) wherein a constant potential difference is maintained between adjacent ring electrodes such that a linear electric field is produced in the axial direction. Alternatively, the use of axially spaced apart electrodes for the drift space (for example ring electrodes or a segmented multipole), may permit application of a so-called 'travelling wave' DC field to separate the ions according to ion mobility, i.e. wherein transient DC voltages are progressively applying along the length of the ion guide comprising the plurality of axially spaced apart electrodes.

An axial electric field generating means is preferably provided to generate an axial electric field along the drift space to drive the ions therethrough. A switchable axial electric field generating means is preferably provided to generate an axial electric field along the drift space to drive the ions in the first or second direction as desired, i.e. to drive the ions in the first direction in one turn and in the second direction in the next turn and so on. In embodiments that do not pass the ions alternately in opposite directions through the drift space but in the same direction on each pass through the drift space, typically it will not require a switchable axial electric field since a static axial electric field could be used. In that case, the ion energy will need to be changed as the ions fly through one of the ion-optical elements in the low-pressure region, e.g. mirror or deflector, by raising its voltage offset of the latter (i.e. by applying an energy lift to the ions) so that ions re-enter the drift space with the correct energy to traverse the drift space again.

For the switchable axial electric field, switching preferably occurs while ions of interest are reflected in the mirror outside of the drift space so that no or minimal perturbation of those ions can take place. The voltage offset of the entire mirror can also be changed at the same time, with ions flying unperturbed inside such a "voltage lift". The direction of the axial field in the drift space is thus preferably switchable between the first and second directions, so as to drive the ions in either the first direction or second direction as required. The axial electric field generating means may be provided, for example, by a plurality or sequence of auxiliary electrodes spaced apart along the drift space length in the axial direction. To such auxiliary electrodes different, preferably stepped, voltages may be provided (preferably with the auxiliary electrodes connected via a resistive divider). Such auxiliary electrodes are preferably located radially outwards of the multipole rods in the case where the ion path through the drift space is provided within a multipole. Alternatively, an axially segmented multipole may be used, i.e. where the segments of the multipole rods provide the mentioned axially spaced electrodes, for example as shown in U.S. Pat. No. 6,111,250. Other means for generating axial electric fields in a multipole ion guide are also known to the skilled person, such as the following: axially spaced ring electrodes as described above, layered RF rods or rods with resistive coatings for example as shown in U.S. Pat. Nos. 7,064,322, 7,164,125 or 7,564,025, shaped surfaces for example as shown in U.S. Pat. No. 6,674,071, and various other means as disclosed in U.S. Pat. No. 6,111,250 such as tapered rods, rods arranged at angles with respect to each other, segmented cases around the multipole rods, resistively coated auxiliary rods, or a set of conductive metal bands spaced along each rod with a resistive coating between the bands, or rods as tubes with a resistive exterior coating and a conductive inner coating. The axial electric field is configured to achieve the desired axial ion velocity. The axial electric field is preferably set so that the axial ion velocity lies in the range 50 to 200 m/s. At pressures in the range 0.01 to 3 mbar, a suitable axial field in the drift space is preferably in the range 0.2 to 10 V/cm to achieve the mentioned ion velocity.

The ions are preferably reflected in the method using an ion mirror. The ion mirror is preferably located adjacent to the drift space, more preferably in a region of lower pressure than the drift space and most preferably in a gas-free region of high vacuum, i.e. where the mean free path of ions in gas is significantly longer than the characteristic length of the mirror or deflector, i.e. the path length in the mirror or deflector measured as the distance from the exit from the drift space to the re-entry to the drift space. This mean free path length between collisions with gas is longer, preferably significantly longer, than the mean free path length in the drift space or spaces. Under such conditions ions stop being entrained in gas, their motion becomes inertial and they obey laws of collision-free ion optics. These regions are thus also termed herein inertial ion motion regions. The ion mirror that reflects the ions that have passed through the drift space, e.g. in the first direction, is preferably located adjacent to a first end of the drift space and may be referred to herein as a first ion mirror (where there are two mirrors as hereinafter described).

In a further preferred embodiment, the method further comprises a step (iv) of reflecting the ions that have passed through the drift space in the second direction followed by passing the reflected ions back through the drift space in the first direction again. In this way the drift space may be utilized at least three times for ion mobility separation of the ions. The ion mirror that reflects the ions that have passed through the drift space in the second direction is also preferably located adjacent to the drift space, more preferably adjacent to a second end of the drift space, which is opposite to the first end. This ion mirror may be referred to herein as a second ion mirror.

The second ion mirror is typically located in a region adjacent to the drift space having a similar pressure regime to the region containing the first ion mirror as described above, i.e. at a lower pressure and most preferably high vacuum. The regions containing the first and optionally second mirrors may share a common gas pumping system, or have separate pumping systems. The regions containing the first and optionally second mirrors preferably have a different pumping system or systems to the pumping system that pumps the drift space since they are at a lower pressure.

Preferably, the second ion mirror is a substantially identical mirror to the first ion mirror but oriented in opposing direction. It will be appreciated that the invention in such embodiments may therefore comprise two opposing ion mirrors located adjacent the opposite ends of the drift space. The ions are preferably reflected in the or each ion mirror through 180 degrees so that after reflection they travel back along the same path, i.e. along the same axis, but in the opposite direction. The arrangement of the drift space and the ion mirror or mirrors thereby provides an ion mobility separator (IMS) of extended path length in which the simple linear drift space is utilized more than once.

It will be appreciated that after the step of passing the ions through the drift space in the first direction again, the ions may, if desired, be reflected once again and passed back through the drift space in the second direction and so on until a required degree of ion separation according to ion mobility has taken place. In other words, after step (iv), the method may comprise repeating steps (iii) and (iv) by turns as many times as required, e.g. a plurality of times. It will be appreciated that the invention in such embodiments may therefore comprise two opposing ion mirrors located adjacent the opposite ends of the drift space, whereby the ions may be repeatedly reflected between the ion mirrors passing through the drift space between each reflection, i.e. in alternating forward and reverse directions.

Each pass through the drift space extends the ion mobility separation length by L, where L is the length of the drift space. The total ion mobility separation path is therefore given by M*L, where M is the number of passes through the drift space. This allows for a practically unlimited increase in resolution of ions by their ion mobility.

The invention also may be implemented using an ion deflector instead of the or each ion mirror. In other words, the invention may be implemented using mirrors and/or deflectors as the ion optics that receive ions from a drift space after a stage of ion mobility separation and direct the ions into the same or another drift space for a further stage of ion mobility separation. For conciseness, certain features of the invention are described herein with reference to the use of ion mirrors. However, it should be understood that the features described with reference to ion mirrors apply mutatis mutandis to embodiments using ion deflectors, wherein for example reflecting of ions changes to deflecting of ions and so on.

1. Within the ion mirror or each ion mirror preferably separation of the ions according to their ion mobility does not occur. The region in which the ion mirror or each ion mirror is contained preferably is at a lower gas pressure, more preferably substantially lower gas pressure, than the drift space. The pressure in the regions of the ion mirrors is preferably at high vacuum and is preferably not greater than $10^{-3}$ mbar and more preferably not greater than $10^{-4}$ mbar. Thus, the ion mirror or each ion mirror is preferably located in gas-free regions, e.g. high vacuum, such that separation of the ions according to their ion mobility does not occur in such regions. The mirrors thus preferably provide substantially collision-free ion optics. Thus, within the ion mirrors, ion separation preferably occurs that is independent of ion cross section but dependent on mass-to-charge ratio (m/z).

The ion mirror or each ion mirror provides an electric field to retard and reflect the ions. The ion mirror or each ion mirror preferably provides a non-linear electric field to reflect the ions, i.e. wherein the electric potential varies non-linearly with distance within the mirror, i.e. in the axial direction. The ion mirror or each ion mirror is typically elongated in the axial direction, i.e. the same as the direction of elongation of the drift space. The electric field provided by the ion mirror or each ion mirror preferably provides time-of-flight focusing of the ions in the axial direction, over the region or regions adjacent the drift space in which the ion mirror or each ion mirror is located. As the object of the ion optical arrangement is the pulsed source of ions which is at the end of the drift tube, the mirror focuses the ions back to this image and so the ions can be temporally focused at the entry of the drift space. The use of a non-linear electric field may provide time-of-flight focusing of the ions over this entire region. In this way, the spatial broadening of the ions outside the drift space in the regions containing the mirror or mirrors is smaller, typically significantly smaller, than the broadening due to diffusion in the drift space where ion mobility separation takes place. This axial energy spread of the ions is likely to be high so that time-of flight focusing in the axial direction by the mirrors is advantageous.

The quality of time of focusing need not be high so that suitable reflecting electric fields include ideal parabolic fields (as described in U.S. Pat. Nos. 4,625,112 and 5,077, 472), polynomial fields (as described in U.S. Pat. Nos. 5,464,985 and 5,814,813) and non-linear fields with additional acceleration (as described in U.S. Pat. No. 6,365,892). Preferably, the ions are accelerated by an accelerator, for example to overcome patch potentials where the pressure drops sharply from the drift space to high vacuum, followed by reflecting the ions in the non-linear electric field. Such accelerating is preferably provided by means of a short region with a small accelerating field (e.g. 1 to 10 V). Thus, the present invention is preferably implemented using a linear axial field or travelling wave within the drift space and a non-linear axial field or fields outside the drift space (i.e. in the ion mirror or mirrors).

The retarding and reflecting electric field of the ion mirror or mirrors is preferably provided by axially spaced apart auxiliary electrodes, e.g. ring electrodes, to which appropriate voltages are applied. At least one or more end auxiliary electrodes at the distal end of the ion mirror typically have a retarding voltage applied. The end auxiliary electrode or electrodes at the distal end of the ion mirror preferably form an end aperture. By modulating the voltage on the end aperture of the ion mirror, ions may be allowed to be extracted through the aperture and thus through the ion mirror. Other means of generating retarding electric fields in ion mirrors are known to the skilled person. The ion mirror or each ion mirror preferably comprises a multipole ion guide.

It is preferred that the offset voltage of at least one of the mirrors, preferably at least the first mirror, is switchable so that it enables the ions to be passed back into the drift tube in the opposite direction from which they entered the mirror, e.g. by ramping the offset voltage as the ions are reflected.

The ions may be introduced into the drift space through the or one of the ion mirrors, i.e. the ions reach the entry to the drift space through the or one of the ion mirrors. For example, where there are two ion mirrors the ions may be introduced through the second ion mirror (i.e. the mirror at which the second reflection takes place). Similar to ion extraction through an ion mirror, ion introduction may be effected by modulating the voltage on an end aperture of the ion mirror.

The invention preferably further comprises, after separating the ions by their ion mobility, extracting ions, for example of selected ion mobility, from the drift space, preferably through one of the ion mirrors. After extracting ions the invention preferably comprises detecting the extracted ions using a detector and/or subjecting the ions to further processing. The extracted ions may be detected using a mass analyzer as a detector, i.e. in a hybrid ion mobility spectrometer-mass spectrometer (IMS-MS) arrangement or may be simply detected using an ion detector, such as an SEM, to provide a simple ion mobility spectrum. Preferably, the extracted ions are subjected to mass analysis using a mass analyzer, e.g. downstream of the ion mobility separator, optionally after ion fragmentation. Further processing of extracted ions may comprise further separation by ion mobility, separation by mass-to-charge, and/or fragmentation.

The extracted ions of selected ion mobility may be subjected to further processing, for example one or more stages of mass separation or analysis (for example MS/MS or $MS^n$), with optionally one or more stages of ion fragmentation. The present invention may be utilized, for example, in various hybrid instrument configurations such as IMS/MS or IMS/MS/MS or IMS/$(MS)^n$. In some embodiments, a mass analyzer of mass filter may be utilized upstream of the IMS to provide, for example, instrument configurations such as MS/IMS/MS, MS/IMS/MS/MS or MS/IMS/$(MS)^n$.

The ion mobility spectrometer of the present invention may be used in various instrument configurations and with various other components, some of which are described below.

An ion source is preferably present for providing the ions for separation in the drift space. The ion source may be any suitable ion source for generating ions, including, for example, an electrospray ion (ESI) source, or a MALDI ion source, especially for biological samples, including mixtures of proteins. The ions are preferably presented to the drift space as a pulse or packet of ions for separation according to their ion mobility.

The ion mobility spectrometer preferably comprises an ion storage device, such as an ion trap, upstream of the drift space so that ions may be introduced from the ion storage device into the drift space, e.g. as a pulse or packet of ions for ion mobility separation to subsequently take place in the drift space. The ion storage device stores ions from the ion source prior to introduction into the drift space. The ion storage device may comprise a multipole for injecting ions into the drift space. The ions may be introduced from the ion storage device into the drift space through an ion mirror. For example, where there are two ion mirrors the ions may be introduced through the second ion mirror (i.e. the mirror at which the second reflection takes place).

Preferably, either the upstream ion storage device or a further ion storage device, such as an ion trap, downstream of the drift space may be used so that ions separated by ion mobility may be extracted from the drift space and stored within the ion storage device. From the ion storage device the extracted ions of selected ion mobility may be subjected to further ion mobility separation in the drift space or may be mass analyzed, e.g. in a mass analyzer downstream of the ion storage device. Alternatively, the ion storage device, for example where it is an ion trap, may be used as a mass analyzer. Where a downstream ion storage device is used, the ions from the downstream ion storage device may be re-introduced back into the upstream ion storage device, for example for further ion mobility separation.

The ion storage device may be a linear ion trap, especially a curved linear ion trap (also known as a C-trap), for example as described in WO 2008/081334. The ion storage device which ejects ions into a mass analyzer such as an orbital ion trap is preferably a C-trap.

A fragmentation cell may be provided to which the ions may be optionally sent to prior to mass analysis. For example, the ion storage device containing ions from the ion mobility separation may optionally send the ions to the fragmentation cell prior to mass analysis. In this way, mass spectra of the ions may be obtained either without fragmentation or with fragmentation, as required.

The mass analyzer may be any suitable type of mass analyzer known in the art, such as an ion trap, for example a linear ion trap, 3D ion trap, electrostatic ion trap, or orbital ion trap (for example an ORBITRAP mass analyzer), a TOF mass analyzer, for example a linear TOF, single reflection TOF, or multi-reflection TOF, a magnetic sector mass analyzer, or a Fourier-transform mass analyzer, for example an FT-ICR mass analyzer.

A mass filter, for example a transmission quadrupole mass filter or ion trap mass filter, may be provided upstream of the drift space for mass pre-filtering of ions from the ion source prior to introduction into the drift space. The mass filter is preferably provided upstream of the ion storage device that in turn is upstream of the drift space so that the mass filtered ions are collected in the ion storage device before introducing the ions from the ion storage device into the drift space. Examples of preferred configurations of the present invention include Q-IMS-TOF and Q-IMS-Orbital trap, where Q represents a quadrupole mass filter.

In one type of operation mode, a mass analyzer may be arranged to detect ions extracted from the ion mobility separator of selected ion mobility having one or a limited number of m/z values (i.e. a narrow m/z band) so that the instrument thereby provides an ion specific detector. In a more typical mode of operation, referred to as a mobility filtering mode, little or no mass filtering is applied or at least a broad range of m/z values are transmitted through the ion mobility separator and a mass spectrum is obtained by a mass analyzer for each of a plurality of narrow ranges of ion mobilities transmitted by the ion mobility separator (i.e. a mass spectrum is obtained for each ion mobility peak or range of mobilities, thereby resolving each single ion mobility peak or range into its m/z components). A two-dimensional (2D) mobility/mass diagram can be obtained in this way.

Another type of operation mode, a so-called linked-scan mode, which allows selection only of ions of certain type(s), e.g. peptides only, which can greatly improve the dynamic range of analysis of complex mixtures and avoid analyzing analytically useless ions (e.g. singly-charged and polymers ions in the case of peptide mixtures). In the linked-scan method, a mass filter, e.g. quadrupole mass filter, is scanned simultaneously with the mobility scanning by the ion mobility separator so that only ions of pre-determined mobility/mass ratio or lying on a pre-determined curve on a mobility/mass diagram are selected for subsequent processing or detection, e.g. mass analysis, with or without an intermediate fragmentation of the selected ions. The selected ions of pre-determined mobility/mass ratio or lying on a pre-determined curve on a mobility/mass diagram in this way are preferably accumulated in an ion trap before subsequent mass analysis (e.g. using an ORBITRAP mass analyzer or a TOF mass analyzer). The space charge capacity of the ion trap can be utilized to the full since only ions of interest are selected and accumulated in the trap.

The ion mobility spectrometer of the present invention may be used with other separation techniques, which preferably take place before the ion mobility separation, such as liquid chromatography IMS (LC-IMS) and gas chromatography IMS (GC-IMS), with or without MS analysis.

The spectrometer and method according to the present invention could be used for field-asymmetric ion mobility spectrometry (FAIMS). The FAIMS field in that case would be applied in the radial direction across the drift space and comprise a periodic asymmetric electric field such that ions flowing axially along the drift space would be caused to separate according to differential ion mobility as known in the art. For this, it is typical to increase E/P in the drift space significantly above 200 V/(m*mbar).

It can be seen from the foregoing description and the more detailed description below that the present invention provides an improved ion mobility spectrometer and method of ion mobility spectrometry. In particular, various embodiments of the present invention may provide one or more of the following: a long ion separation length within a limited space; an ion separation length which can be varied depending upon the number of ion reflections employed; an ion mobility spectrometer with a long ion separation length provided by a simple design; an ion mobility spectrometer easily switchable between modes of different ion separation resolution and speed; and a method of filtering ions based on their ion mobility coupled with analysis using a mass spectrometer, especially an ion trap mass spectrometer.

DETAILED DESCRIPTION OF THE INVENTION

In order to more fully understand the invention, it will now be described by way of non-limiting example with reference to the accompanying drawings in which.

Figure 1:
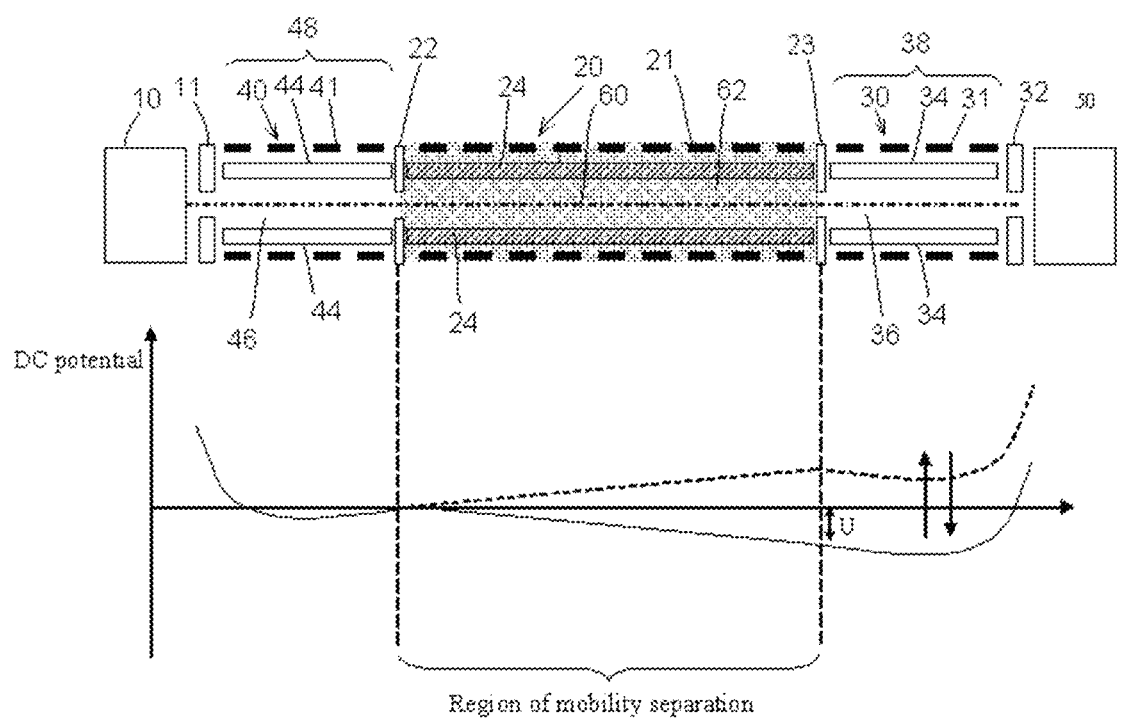
FIG. 1 shows schematically an embodiment of an ion mobility spectrometer according to the present invention.

Referring to FIG. 1, there is shown schematically in side view an embodiment of an ion mobility spectrometer according to the present invention. Ions from an ion source (not shown), or optionally from a previous stage of mass analysis or other ion processing (not shown), are initially stored in an ion storage or trapping device 10. This trapping device may be, for example, a multipole ion trap, which, in turn, may be a C-trap. In use, the trapped ions are ejected as a short packet or pulse from trapping device 10 in a first or forwards direction towards a drift space, which in this example is located within a gas-filled RF multipole 20 located downstream of the trapping device 10. The ions travel through an entrance aperture 22 at the upstream end of the multipole 20 to enter the multipole 20. In the embodiment shown, the ions also first pass through a first aperture 11 and an ion mirror 48 contained in a gas free region 46 each located upstream of the entrance aperture 22, which are described in more detail below. In other embodiments, the ion mirror 48 may not be present (for example where only a single reflection of the ions is used). Where used, the aperture 11 may have a voltage applied to it modulated to allow ions to pass from ion trapping device 10 through the ion mirror 48 and into the gas-filled multipole 20.

The gas-filled RF multipole 20 comprises elongated multipole rods 24, for example four such rods in the case of a quadrupole, and is elongated in an axial direction with a central longitudinal axis 60 running through it in the axial direction. In some embodiments, as described below, the multipole may have a mass resolving DC voltage applied to it, for example to enable it to filter out some unwanted ions from the start. Typically, the inscribed radius of the rods is from 2 to 4 mm and the rod length is from 100 to 500 mm. The drift space is located inside the multipole rods 24. The rods are provided with an RF voltage (typically 500 to 3000 V peak-to-peak at 1 to 5 MHz) to constrain the ions radially and guide the ions as they move axially through the drift space within the multipole. The multipole 20 is provided in use with a switchable axial electric field to drive the ions in the axial direction, which in the example shown in the drawing is provided by means of axially separated auxiliary electrodes 21 that are located adjacent and radially outwards of the multipole rods 24. The electrodes 21 are preferably connected via a resistive divider (not shown) to provide the desired potential gradient. In other embodiments the axial electric field may be provided by other means. In FIG. 1, the DC potentials applied within the various regions of the ion mobility spectrometer are shown schematically below the drawing of the spectrometer. The solid line represents the DC potential curve for a pass in the first/forward direction through the spectrometer for the case of positively charged ions. The dotted line represents the DC potential curve for a pass in the second/reverse direction through the spectrometer as described in more detail below. It will be appreciated that the present invention can be applied to the separation of either positively or negatively charged ions by reversing the potentials.

The multipole 20 is contained in a gas-filled region which is indicated in the drawing by the hatched region 62. The pressure in the region 62 of the multipole 20 is preferably in the range 0.01 to 3 mbar and the axial field is preferably about 0.2-10 V/cm so that the axial ion velocity in the gas filled drift space preferably lies in the range 50-200 m/s. In use, the ions separate according to their ion mobility as they move axially through the drift space within the gas-filled multipole. Each pass through the drift space separates the ions with a resolving power R1 of about 5 to 20.

In use, after the ions have made their first pass axially through the drift space within multipole 20 in the first or forward direction and thereby undergone a first degree of separation by ion mobility, they exit the gas-filled region 62, in this embodiment through exit aperture 23, and enter into a gas-free region 36 containing a first ion mirror 38 for reflecting the ions. The gas-free region in practice means a region at a vacuum which is at least high vacuum (preferably less than $10^{-3}$ mbar, more preferably less than $10^{-4}$ mbar). The ion mirror 38 comprises an RF multipole 30 elongated in an axial direction and comprising elongated multipole rods 34, for example four such rods in the case of a quadrupole. The ions enter the first ion mirror 38 and travel within the multipole 30 where they experience reflection by a retarding axial electric field provided by appropriate voltages applied to axially spaced apart auxiliary electrodes 31, which are located radially outward of the multipole rods 34, as well as end aperture 32. The DC potential of the retarding field of the mirror is shown by the solid line below in FIG. 1. The total length of the mirror is typically from 50 to 200 mm.

Preferably, the retarding electric field of the ion mirror provides focusing of the ions on time-of-flight over the entire gas-free region 36 in which the ions travel so that when they return back to the drift space within the gas-filled multipole 20, the spatial broadening of the ion packet $\Delta_{TOF}$ due to time of flight is significantly smaller than broadening of the packet $\Delta_{IM}$ due to diffusion in the ion mobility region, i.e. the drift space. This can be represented as follows:

$$\Delta_{TOF} \ll \Delta_{IM} = L\sqrt{\frac{kT}{ezU}} = \frac{L}{2 \cdot R1}$$

wherein L is the length (m) of the ion mobility separation path in the gas-filled region (drift space); U is the potential drop (V) along the drift space, i.e. along the axis of the multipole 20; z is the charge state of ions; T is the temperature (K) of the gas in the gas filled region; e is the elementary charge ($1.602 \times 10^{-19}$ Coulomb); and k is Boltzmann's constant ($1.38 \times 10^{-23}$ J/K). As ions are thermalized at the exit from multipole 20, their energies range from a few mV up to 50-100 meV and therefore their relative axial energy spread is high. It is possible to provide time-of-flight focusing in spite of such energy spreads if non-linear fields are used for the reflection of ions so that time-of-flight focusing takes place on the re-entry into multipole 20. The required quality of such focusing is not very high, so acceptable fields for this purpose range from ideal parabolic fields (see for example those described in U.S. Pat. Nos. 4,625,112 and 5,077,472) to polynomial fields (see for example those described in U.S. Pat. Nos. 5,464,985 and 5,814,813), as well as non-linear fields with additional acceleration (see for example those described in U.S. Pat. No. 6,365,892). A particularly preferable field for the ion mirror would be provided by a short region having a very small accelerating axial field to overcome patch potentials where the pressure reduces sharply down to high vacuum, this region being followed by reflection in a parabolic field, for example according to U.S. Pat. No. 4,625,112.

In view of the low axial energies, it is preferable that patch potentials on electrodes of multipole 30 are minimized as described for example in our co-pending application number GB 1116837.4 filed on 30 Sep. 2010. In this embodiment, heating and/or the use of uniform coatings to reduce patch potentials could be implemented for the entire assembly.

To reduce additional scattering of the ion beam on the exit from the gas-filled multipole 20, one or both its end apertures 22 and 23 could be configured to provide a barrier for gas but not interrupt the continuity of the RF field. Preferably, the end apertures of the gas-filled multipole have RF applied to them. An example of such apertures is shown schematically in FIG. 2 for a particular case of a quadrupolar field. The aperture is shown end-on and comprises four conductive segments or fingers 28, separated by small gaps x, in which opposite pairs are electrically connected with the same phase of RF (i.e. a first pair of opposite segments having a phase 1 of RF and a second pair of opposite segments having a phase 2 of RF, where 1 and 2 are opposite phases of RF) to provide the quadrupolar field. The ions pass through radially central aperture 27 in the segments through which the central axis 60 of the system runs. In general, for a 2N-polar field (N=2 for quadrupole, N=3 for hexapole, N=4 for octapole, etc.), the apertures 22 and/or 23 could be constructed with 2N segments separated by small gaps. For a 2N-polar field, the apertures 22 and/or 23 could be constructed as metal-coated PCBs with 2N segments or fingers separated by small gaps (e.g. gap distances of about 0.5 mm). Preferably, the amplitude of the RF on the aperture 22, 23 is smaller than the RF on the 2N-pole (in this case the quadrupole 20) and more preferably it is smaller by a factor equal to the N-power of the ratios of the effective radii. This could be achieved by providing capacitively-matched dividers. By an "effective radius" is meant the inscribed radius of an ideal multipole that would create the same field structure on the central axis as the actual construction. For example, for a flatapole, the effective radius is smaller than half of the gap between the electrodes. For an aperture of the type shown in FIG. 2, the effective radius is even further reduced relative to its actual radius because the edges of each quadrant come closer to the axis, rather than bending away as in an ideal quadrupole.

The retarding field provided by the first ion mirror 38 reflects the ions as described above so that they return backwards towards the gas-filled multipole 20 for a second pass through the drift space contained therein. As ions return towards multipole 20, the DC offset voltage of the first ion mirror, i.e. multipole 30, as well as the end of the chain of auxiliary electrodes 21 along the drift space closest to the first mirror, is ramped up, as shown by the dotted line in the potential plot in FIG. 1. This ramping should be strictly synchronized so that ion motion is not perturbed. In this way, upon re-entry to the drift space the ions find themselves in continuing ion mobility separation travelling in the reverse or second direction through the drift space. Thus, the axial field along the drift space within the gas-filled multipole 20 is reversed. As the ions reach the other end of the gas-filled multipole 20, they exit the gas-filled drift space and enter into gas-free region 46 containing a second ion mirror 48 for reflecting the ions. This gas-free region in practice again means a region at a vacuum which is at least high vacuum (preferably less than $10^{-3}$-$10^{-4}$ mbar). The ions are reflected in the same manner in the second ion mirror 48, which is substantially identical to the first ion mirror 38 but oriented in the opposing direction to the first ion mirror, and comprises a gas-free multipole 40 having elongated multipole rods 44. The second ion mirror 48 is supplied with a similar but oppositely directed retarding axial field as the first mirror. The retarding field of the second mirror is provided via axially spaced apart auxiliary electrodes 41, which are located radially outward of the multipole rods 44, as well as end aperture 11. The main difference is that this time there is no need to change the DC offset of multipole 40 as the ions are reflected but only the end of the chain of auxiliary electrodes 21 along the drift space, which needs to be ramped back down (see the solid line in the potential plot) to the condition initially used on the first pass through the drift space in the forward direction. The ions then re-enter the drift space within gas-filled multipole 20 to travel through it again in the first or forward direction. In this way, the whole ion mobility separation process may be started over again.

Whilst in the embodiment shown in FIG. 1, the multipoles 20, 30 and 40 comprises their own set of rods 24, 34 and 44 respectively, in some embodiments the rods 24, 34 and 44 could be physically the same set of rods such that the multipoles 20, 30 and 40 are different sections of the same set of rods. In such embodiments, the apertures 22 and 23 may be intricately installed in-between the sections constituting multipoles 20, 30 and 40. Some of the rods could be split for this purpose. Some rods could be physically the same for all multipoles and some could be split. One of the multipoles could comprise its own set of rods and two of the other multipoles could be physically the same set of rods.

The process of reflecting the ions and passing them through the drift space is repeated multiple times until the separation of the ions of interest according to their ion mobility reaches desired levels (roughly proportional to the square root of number of passes M). Each pass through the drift space typically separates the ions with a resolution R1 of about 5 to 20. At the ends, ions with a selected one ion mobility or range of ion mobilities can be filtered out by modulating voltages on the end apertures 11 or 32 so that the selected ions exit therethrough, i.e. exit through either ion mirror by modulating the retarding field of the mirror to a non-retarding condition. Selected ions that exit through upstream end aperture 11 can be trapped in the upstream ion storage or trapping device 10. Selected ions that exit through the downstream end aperture 32 can be trapped in downstream ion storage or trapping device 50.

Ions separated by ion mobility and subsequently stored in either of the trapping devices 10 or 50 may be ejected to a mass analyzer for mass analysis or for other ion processing depending on the instrument configuration. The trapping devices 10 or 50 may be a linear ion trap, especially a curved linear ion trap (C-trap) for this purpose.

To remove ions of higher mobility, the voltage on aperture 32 could be modulated (lowered if considering positively charged ions) while ions of interest are still inside multipole 20. Ions of lower mobility remain inside multipole 20 during the entire separation and they might create space charge effects negatively affecting the quality of mobility separation of ions of interest. To remove ions of lower mobility, RF on multipole 20 could be occasionally switched off or resolving DC applied to the rods of multipole 20 in the case of a quadrupole configuration. Optionally, resolving DC could be also used during the entire mobility separation to provide rapid removal of unwanted species or any products of ion-molecule reactions.

In an alternative embodiment of the present invention, a deflector, such as a 180 degrees toroidal electric sector, could be used instead of a reflecting ion mirror to return the ions in the opposite direction with TOF focusing, the deflector preferably being in a gas-free region as for the case of the ion mirror described above. An example of this configuration is shown schematically in FIG. 3A. Ions from storage device 10 are introduced along first axis 70 through a gas free region containing a toroidal electric sector deflector 90 into a gas-filled drift space 72 wherein ion mobility separation occurs. The deflector 90 has an aperture (not shown) to allow the ions to pass through it from the storage device 10 an into the drift space 72. The ions also pass through a first one of four short ion guides 71 positioned between the drift space 72 and the deflector 90. The ions are guided along first axis 70 in the drift space by first RF multipole 74, wherein an axial DC field urges the ions along the axis 70. The shaded area 82 represents the total gas-filled drift space region. Such embodiments may return the ions along an axis in the reverse direction that is parallel to the axis followed in the forward direction but displaced from it. A similar deflector in a similar gas-free region at the other end of the drift space would deflect ions through 180 degrees to return the ions along an axis in the opposite direction. In the shown case, a similar toroidal electric sector deflector 100 to deflector 90, also in a gas-free region, receives ions that have traveled along the first axis 70 and returns them with time-of-flight focusing to travel in the opposite direction along second axis 80, which is parallel to but displaced from first axis 70. Each axis would be designed to have its own ion guide, e.g. there would be two parallel ion guides. Thus, the ions are guided along second axis 80 in the drift space by second RF multipole 84, wherein an axial DC field urges the ions along the axis. Ions thereafter enter the first deflector 90 and are deflected through 180 degrees and time-of-flight focusing back onto first axis 70 and into the drift space again and so on. This would mean that the DC field could be kept in one direction along the first (forward) axis 70 and kept in the opposite direction on the second (reverse) axis 80. Matching of potentials could be achieved by a voltage lift of the ions inside one or both deflectors, or by shifting the voltage distributions inside the ion guides as described in the embodiment above. In this embodiment, it can be seen that two separate ion paths are defined along respective axes 70 and 80, each path lying within its own respective multipole 74 and 84 and both being provided within a single gas filled drift space 82 to provide two paths of ion mobility separation. In this embodiment, as with the embodiments above using ion mirrors, within the ion deflector separation of the ions according to their ion mobility does not occur. The ion mirror or ion deflector are preferably located in gas-free regions, e.g. high vacuum, such that ion mobility separation of the ions does not occur in such regions. Such ion mirrors or deflectors preferably provide time-of-flight focusing of the ions across their regions. Other features herein described in relation to the embodiments of the invention using ion mirrors are applicable mutatis mutandis to the further embodiments of the invention using ion deflectors. Ions, for example, are could be extracted through one of the deflectors 90 or 100, e.g. through an aperture therein, once the ions of interest are sufficiently separated by ion mobility.

Figure 3A:
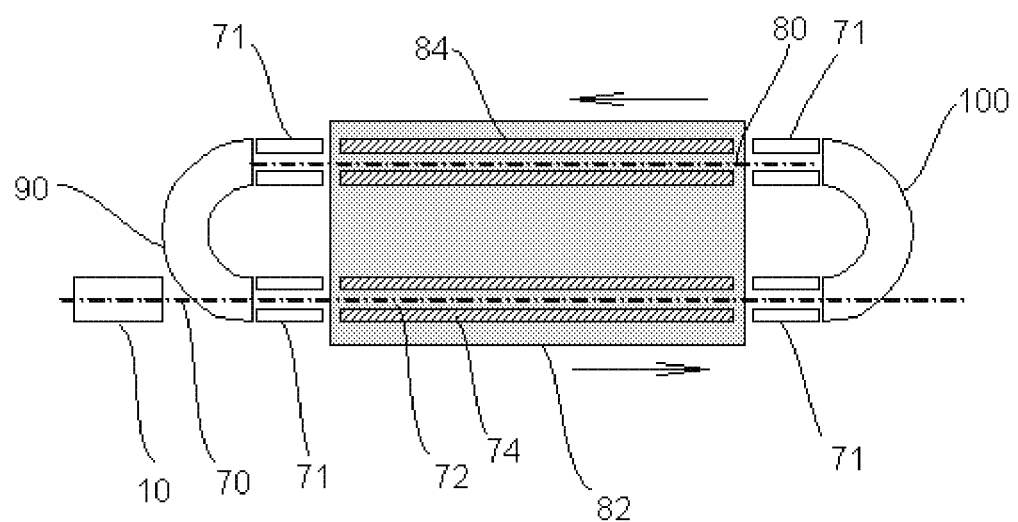
FIG. 3A shows schematically another embodiment of an ion mobility spectrometer according to the present invention.
Figure 3B:
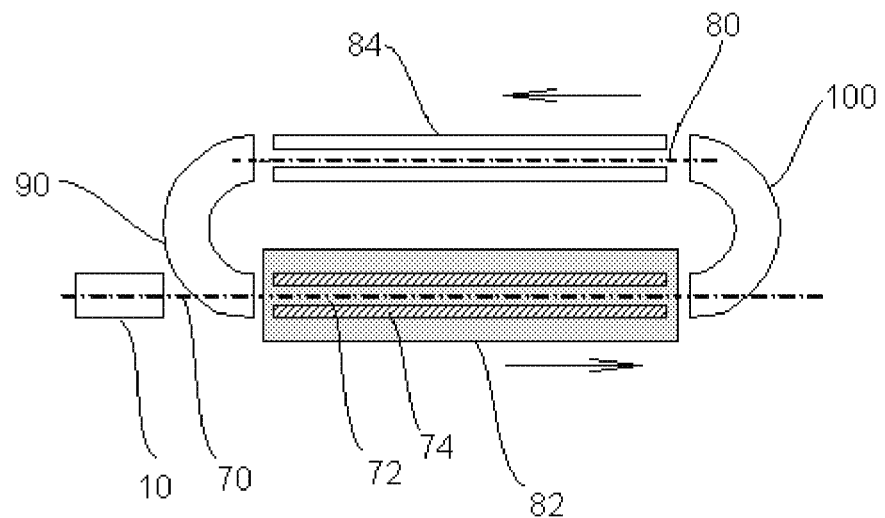
FIG. 3B shows schematically a further embodiment of an ion mobility spectrometer according to the present invention.

A further embodiment of the present invention is shown schematically in FIG. 3B, which is largely similar to the embodiment shown in FIG. 3A such that like references denote like components. In the embodiment shown in FIG. 3B, only one ion mobility separation path along axis 70 is provided in a smaller gas filled drift space 82. The ions pass for a first time through the drift space 82 from its entry to its exit and then are returned via ion optics comprising the deflector 100, straight multipole 84 and deflector 90 back to the entry where they can pass once again through the gas filled drift space 82 and so on. The returning ion optics are contained in a high vacuum region as before.

Figure 3C:
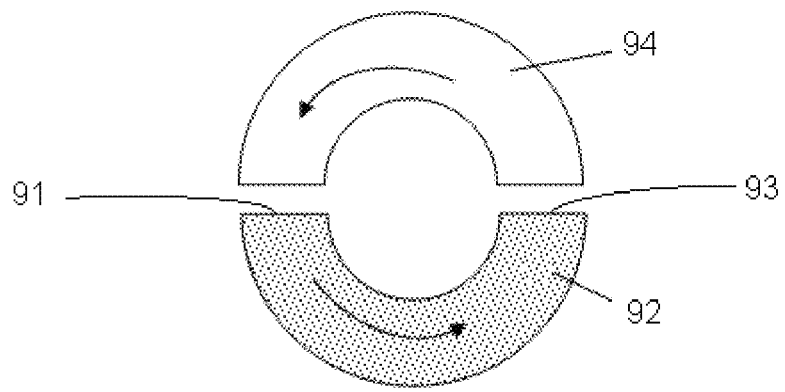
FIG. 3C shows schematically still another embodiment of an ion mobility spectrometer according to the present invention.

FIG. 3C shows schematically still another embodiment of an ion mobility spectrometer according to the present invention wherein two opposing 180 degree toroidal electric sectors are utilized to provide a curved, generally circular, ion path. In this embodiment, a drift space comprises a gas-filled 180 degree toroidal sector 92 having an entry 91 and exit 93. The direction of ion motion is denoted by the arrows. The ions are received from the exit 93 of the drift space into a gas-free 180 degree toroidal sector 94 wherein the ions undergo inertial motion. Ions are then returned once more with time of flight focusing to the entry 91 of the drift space. As many passes through the gas filled sector are performed as are required until the desired resolving power has been reached. Ions may, for example, enter the drift space or gas free region through an aperture (not shown) in either of the sectors 92, 94 to begin motion along the ion path shown. Similarly, the ions of interest may be extracted through one of the sectors after separation by ion mobility has taken place to the required degree. In other embodiments, other curved paths may be provided, e.g. within a curved RF multipole.

Various modes of operation of the ion mobility spectrometer are possible, such as the following for example:

1.) A high-resolution mode, as described above, wherein a narrow range of ion mobilities is zoomed in and a total ion flight length is L*M, while the ion mobility range is reduced by factor M.

2.) A low-resolution mode, wherein ions are allowed to fly through the system without reflection (M=1) and ions of interest could be gated into the storage device 50 by modulating the voltage on end aperture 32 and trapped there. From there the ions could be transferred back (if needed) to upstream ion storage device 10 for further ion mobility separation, or they could be mass analysed in a mass analyser.

3.) A so-called augmented mode, wherein one range of ion mobilities is analysed by a high- or low-resolution method and ions of desired ion mobility are filtered into the ion storage device 50. Then further ranges of ion mobility are analysed, each time desired ions being allowed to enter ion storage 50. After that, ions could be transferred downstream (e.g. for mass analysis or further processing) or upstream into ion storage device 10 for (further ion mobility separation). As an alternative to directing to enter ion storage 50, the selected ions could be directed into ion storage 10 and from there the ions could be transferred for mass analysis or further processing or further ion mobility separation.

4.) A fragmentation mode, wherein the offset of one of the multipoles could be raised so high that ions undergo fragmentation in the drift space of gas-filled multipole 20. This could be followed by another ion mobility separation or other further processing or mass analysis.

5.) A transmission mode, wherein ions are allowed to drift along the device in a quasi-continuous manner, being pulled by the axial field between devices 10 to 50.

6.) A multiplexed mode, wherein one or more additional pulses of ions are injected from the ion storage 10 into the drift space so as to be in synchronisation with ions of interest (for example injecting the or each additional pulse just after the ions of interest experience reflection in mirror 48 each time). This is especially effective when ions of interest have low intensity but a high incoming ion current makes space charge effects noticeable. This mode allows a great increase in duty cycle for long separations of up to >50%.

It will be appreciated that other modes of operation are also possible.

Figure 2:
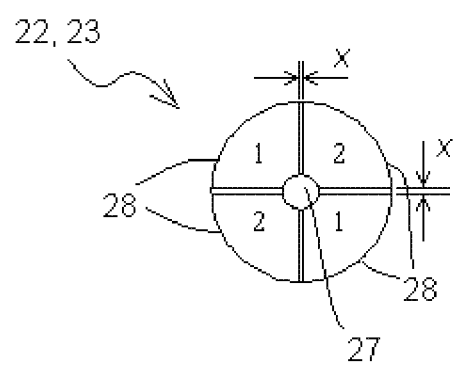
FIG. 2 shows schematically an embodiment of an RF aperture for use in the present invention.

It will be further appreciated that the invention may be implemented using various alternative means to those specifically shown in FIGS. 1 and 2. For example, instead of the multipoles 20, 30 and 40, ion tunnels, ion funnels and/or other devices could be used in place of any or each of them, with or without RF applied. Furthermore, instead of using a DC axial gradient field for the ion mobility separation, a travelling wave could be used as known in the art and as referenced above.

Figure 4A:
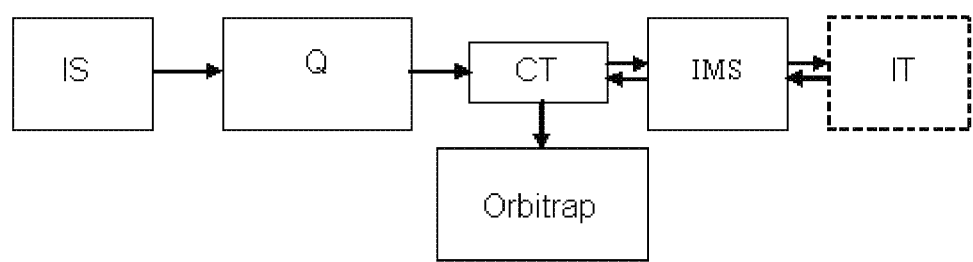
FIGS. 4A and 4B show schematically two respective embodiments of hybrid IMS-MS systems using an IMS according to the present invention.
Figure 4B:
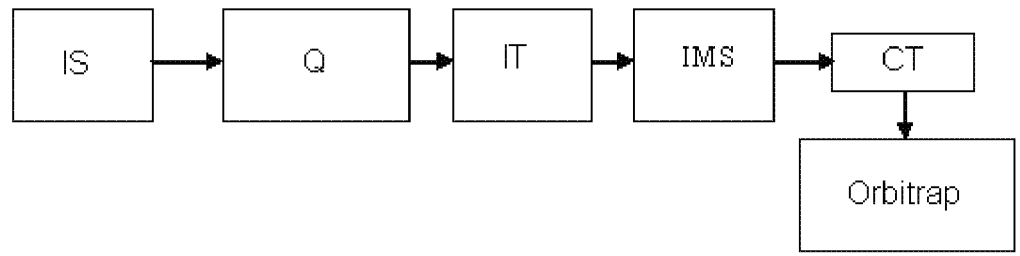

FIGS. 4A and 4B show embodiments of preferred MS/IMS/MS hybrid instruments, which may be a Q/IMS/Trap or Q/IMS/ORBITRAP configuration. In the configurations shown in FIGS. 4A and 4B, the references have the following meanings: IS denotes an ion source; Q denotes a quadrupole mass filter; CT denotes a C-trap; ORBITRAP denotes an ORBITRAP mass analyzer; IMS denotes an ion mobility separator according to the present invention comprising the drift space and opposing ion mirrors (e.g. as shown in FIG. 1); IT denotes an ion store or trap. Other preferred MS/IMS/MS hybrids may use a TOF mass analyzer in place of the ORBITRAP mass analyzer.

The FIG. 4A layout of MS/IMS/MS has the IMS in a 'dead-end' position, wherein ions separated by ion mobility are returned upstream before being mass analyzed in the ORBITRAP mass analyzer. The FIG. 4B layout of MS/IMS/MS has the IMS in an 'in-line' configuration, wherein ions separated by ion mobility are mass analyzed in the ORBITRAP mass analyzer downstream of the IMS.

A C-trap may perform the function of either of the trapping devices 10 or 50 in the FIG. 1 embodiment, especially with an additional axial field inside it. The C-trap may then eject ions to a mass analyzer as known in the art. Instead of an ORBITRAP mass analyzer, any other mass analyzing ion trap, electrostatic ion trap, FT-ICR mass analyzer, or TOF mass analyzer could be used.

It will be appreciated that other configurations are possible such as coupling two or more of the ion mobility separators according to the present invention together in series. For example, selected ions extracted from one ion mobility separator device according to the present invention could be transmitted or introduced into a second ion mobility separator connected in series to the first device and so on to achieve higher degrees of separation according to ion mobility.

Figure 5:
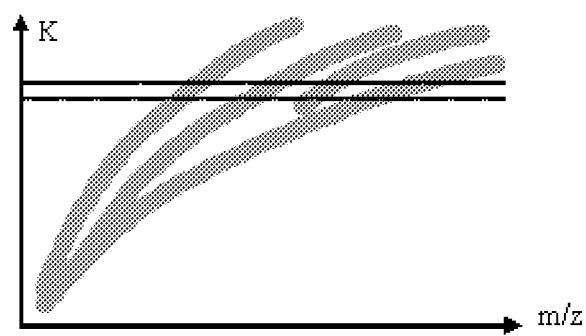
FIG. 5 shows a two-dimensional (2D) mobility/mass diagram which can be obtained using an embodiment of the present invention.

In one type of operation mode, a mass spectrometer may be arranged to detect ions extracted from the IMS of selected mobility having one or a limited number of m/z values so that the instrument thereby provides an ion specific detector. In a more typical mode of operation, a mass spectrum is obtained by a mass spectrometer for each narrow range of ion mobilities transmitted by the IMS (i.e. for each ion mobility peak), thereby potentially resolving a single ion mobility peak into its m/z components. In a preferred mode of operation, there is no mass pre-filtering and the ion mobility spectrometer (IMS) is operated in a filtering mode described above so that it transmits ions of only a narrow range of ion mobilities, K, albeit with a high duty cycle. Referring to FIG. 5 this narrow range of ion mobilities K (i.e. between the dotted lines in the Figure) is shown on a mobility/mass plot of K against m/z. The subsequent mass analyzer, such as an ORBITRAP mass analyzer, receives the ions in the narrow range of ion mobilities and performs a mass analysis, i.e. an m/z scan. For example, using the hybrid instrument shown in FIG. 4A or 4B the quadrupole mass filter (Q) can be operated in RF-only mode so as not to provide mass pre-filtering and the ions in the narrow range of mobility are extracted and stored in the C-trap and then ejected into the ORBITRAP mass analyzer for the mass analysis to be performed. Subsequent scans by the ion mobility spectrometer to transmit further ranges of ion mobilities, K, are then performed and mass analysis is performed for each mobility scan so that a two-dimensional (2D) mobility/mass diagram can be obtained as shown in FIG. 5. Regions of the mobility/mass plot where ion species are detected are shown in FIG. 5 by the shaded bands. Using the known correlation between K and m/z as shown in FIG. 5, analysis speed could be increased by combining several values of K into one mass spectrum, e.g. by accumulating ions of several values of K in the C-trap before analyzing them together in the ORBITRAP mass analyzer. In addition, as described above, fragmentation in a fragmentation cell could be used to create fragments of selected ions.

Figure 6:
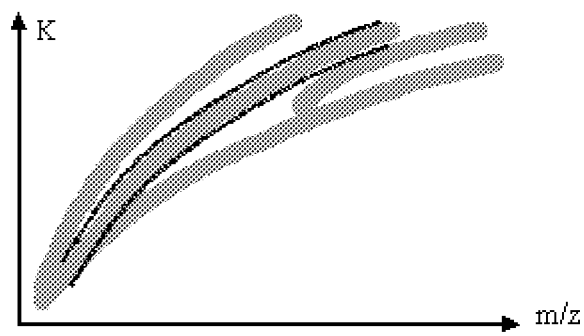
FIG. 6 shows a mobility/mass diagram with a set mobility/mass ratio indicated, which can be scanned in a linked-scan method that may be performed using the present invention.

Another preferred method is illustrated with reference to FIG. 6. In this so-called linked-scan method, it allows selection only of ions of certain type(s), e.g. of selected charge states, which can greatly improve the dynamic range of analysis of complex mixtures and avoid analyzing analytically useless ions (e.g. singly-charged and polymers ions in the case of peptide mixtures). In this linked-scan method, a mass filter, such as the quadrupole mass filter in FIG. 4A or 4B for example, is scanned simultaneously with the mobility scanning by the IMS so that only ions of defined mobility/mass ratio or lying on a defined curve on a mobility/mass diagram are passed into a subsequent mass analyzer, such as the ORBITRAP mass analyzer for example. Prior to the latter mass analysis stage, the ions selected by the defined mobility/mass ratio are preferably accumulated, most preferably in an ion trap, e.g. such as the C-trap in FIG. 4A or 4B. The accumulated ions can then be released from the trap into the mass analyzer. In FIG. 6, a representative mobility/mass ratio accumulated in the C-trap in one scan is shown between the dotted lines. As mentioned, at the end of the scan, all of the accumulated ions can be mass analyzed, e.g. injected into the ORBITRAP mass analyzer and the mass spectrum acquired. In such an operation, a high-resolution mass spectrum, such as obtained using an ORBITRAP mass analyzer or other high resolution type analyzer such as TOF, can be obtained which will include only ions of interest (e.g. 2- or 3-charged ions, or glycopeptides only, etc.) and therefore the space charge capacity of the trap is utilized to the full. In a similar manner, one or more subsequent scans can be taken at different mobility/mass ratios. The mass resolution of the mass filter could be chosen to be similar to that of the IMS so that overall duty cycle remains respectable (e.g. 1-2%). Optionally, mass filtering could be combined with IMS separation by applying resolving DC to the quadrupole rods 24 of the multipole 20.

In addition, certain selected m/z could be fragmented in an optional fragmentation cell to provide fragments for confirmation of a corresponding precursor ion. Optionally, multipole 20 could be used as such a cell, with the energy of collisions being provided by an appropriate amplitude of "voltage lift" applied to the multipole.

Although, the invention is particularly well optimized for use with ion trapping mass analyzers, it could be used with other types of mass analyzers such as TOF analyzers.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A method of ion mobility spectrometry wherein ions undergo multiple stages of ion mobility separation in a drift space region and multiple stages of inertial ion motion wherein the mean free path between ion collisions with gas is longer than in the stages of ion mobility separation, wherein each stage of inertial ion motion lies between successive stages of ion mobility separation to reflect or deflect ions back through the drift space region for a next stage of ion mobility separation to increase ion mobility separation until a desired level is achieved, a drift time separation is maintained between the ions in the stages of inertial ion motion.

2. A method as claimed in claim 1, wherein the ions are reflected by an ion mirror or deflected by a deflector in regions of inertial ion motion.

3. A method as claimed in claim 2 wherein the ions are reflected or deflected by a non-linear electric field.

4. A method as claimed in claim 3 wherein the non-linear electric field provides time of flight focusing of the ions.

5. A method as claimed in claim 3 wherein the non-linear electric field is a parabolic field or polynomial field.

6. A method as claimed in claim 3 further comprising accelerating the ions immediately prior to reflecting or deflecting them in the non-linear electric field.

7. A method as claimed in claim 2 wherein the regions of inertial ion motion are at lower pressure than a drift space where the ion mobility separation occurs, wherein the regions of inertial ion motion are adjacent to opposite ends of the drift space for reflecting or deflecting the ions at each end of the drift space.

8. A method as claimed in claim 7 wherein the drift space is filled with a buffer gas and the regions of inertial ion motion are contained is at high vacuum.

9. A method as claimed in claim 1 further comprising extracting ions from a drift space where the ion mobility separation occurs after separating them by their ion mobility.

10. A method as claimed in claim 9 wherein the ions are extracted from the drift space through an ion mirror or ion deflector.

11. A method as claimed in claim 9 further comprising storing the extracted ions in an ion storage device prior to further processing comprising one or more of: further ion mobility separation, ion fragmentation and mass analysis.

12. A method as claimed in claim 1 wherein the ions are introduced into a drift space where the ion mobility separation occurs through an ion mirror or an ion deflector.

13. An ion mobility spectrometer comprising: one or more drift spaces for separating ions according to their ion mobility; and one or more regions for allowing the ions to undergo inertial ion motion wherein their mean free path between collisions with gas is longer than in the one or more drift spaces, wherein each of the one or more regions is configured to receive the ions from one of the one or more drift spaces and comprises ion optics to reflect or deflect the ions into the same or another one of the one or more drift spaces, whereby each of the one or more drift spaces is arranged to be passed through multiple times by the ions and a drift time separation is maintained between the ions in the stages of inertial ion motion to increase ion mobility separation until desired level is achieved.

14. An ion mobility spectrometer as claimed in claim 13 wherein each of the one or more inertial ion motion regions contains an ion mirror or deflector.

15. An ion mobility spectrometer as claimed in claim 14 wherein the pressure in the inertial ion motion region(s) is such that separation of the ions according to their ion mobility does not occur in such region(s) but separation occurs that is independent of ion cross section but dependent on mass-to-charge ratio (m/z).

16. A ion mobility spectrometer as claimed in claim 14 wherein the ion mirror or deflector provides a non-linear electric field to reflect or deflect ions.

17. A ion mobility spectrometer as claimed in claim 16 wherein the non-linear electric field provides time of flight focusing of ions.

18. An ion mobility spectrometer as claimed in claim 14 wherein the ion mirror or ion deflector is for receiving ions that have passed through the drift space in a first direction and reflecting or deflecting the ions back into the drift space to pass through the drift space in a second direction opposite to the first direction.

19. An ion mobility spectrometer as claimed in claim 18 wherein the ion mirror or deflector is a first ion mirror or deflector and the spectrometer further comprises a second ion mirror or deflector for receiving ions that have passed through the drift space in the second direction and reflecting or deflecting the ions back into the drift space to pass through the drift space in the first direction again.

20. An ion mobility spectrometer as claimed in claim 19 wherein the two mirrors or deflectors constitute two opposing ion mirrors or deflectors located adjacent the opposite ends of the drift space, whereby the ions may be repeatedly reflected or deflected between the ion mirrors or deflectors passing through the drift space between each reflection or deflection.

21. An ion mobility spectrometer as claimed in claim 13 wherein the drift space is contained within a multipole.

22. An ion mobility spectrometer as claimed in claim 13 wherein in use the drift space is filled with a buffer gas and the one or more inertial ion motion regions are held at high vacuum.

23. An ion mobility spectrometer as claimed in claim 13 further comprising an ion storage device upstream of the drift space for storing ions from the ion source prior to introducing them as a pulse of ions into the drift space.

24. An ion mobility spectrometer as claimed in claim 23 wherein the upstream ion storage device is also for storing ions extracted from the drift space after ion mobility separation has taken place.

25. An ion mobility spectrometer as claimed in claim 23 further comprising an ion storage device downstream of the drift space for storing ions extracted from the drift space after ion mobility separation has taken place.

26. An ion mobility spectrometer as claimed in claim 23 further comprising a mass analyzer for mass analyzing ions extracted from the drift space after ion mobility separation has taken place.

* * * * *

UNITED STATES PATENT AND TRADEMARK OFFICE
CERTIFICATE OF CORRECTION

PATENT NO. : 9,753,011 B2  
APPLICATION NO. : 14/947119  
DATED : September 5, 2017  
INVENTOR(S) : Alexander A. Makarov Page 1 of 1

It is certified that error appears in the above-identified patent and that said Letters Patent is hereby corrected as shown below:

In the Claims

Claim 13, Column 20, Line 35/36:  
Replace "to increase ion mobility separation until desired level is achieved"  
With --to increase ion mobility separation until a desired level is achieved--

Signed and Sealed this  
Third Day of April, 2018

Andrei Iancu  
*Director of the United States Patent and Trademark Office*